United States Patent [19]
Hess et al.

[11] Patent Number: 5,058,573
[45] Date of Patent: Oct. 22, 1991

[54] ELASTIC WRIST BANDAGE

[75] Inventors: Heinrich Hess, Saarlouis; Wolfgang Krause, Kassel; Hans B. Bauerfeind, Kempen, all of Fed. Rep. of Germany

[73] Assignee: Bauerfeind GmbH and Co., Kempen, Fed. Rep. of Germany

[21] Appl. No.: 434,998

[22] Filed: Nov. 9, 1989

[30] Foreign Application Priority Data

Nov. 14, 1988 [DE] Fed. Rep. of Germany ....... 3838564

[51] Int. Cl.⁵ ................................................. A61F 5/10
[52] U.S. Cl. ....................................... 128/77; 128/155
[58] Field of Search ...................... 128/77, 80 C, 84 R, 128/87 R, 155, 165, 166; 273/54 B

[56] References Cited

U.S. PATENT DOCUMENTS

| | | | |
|---|---|---|---|
| D. 239,220 | 3/1976 | Norman | 273/54 B X |
| 3,146,463 | 9/1964 | Wargo | 128/166 X |
| 3,189,919 | 6/1965 | Chase | 128/165 X |
| 3,595,575 | 7/1971 | Gooch | 273/54 B |
| 3,990,440 | 11/1976 | Gaylord, Jr. | 128/165 X |
| 4,034,979 | 7/1977 | Wester | 273/54 B |
| 4,040,632 | 8/1977 | Pawl | 273/54 B X |
| 4,047,250 | 9/1977 | Norman . | |
| 4,584,993 | 4/1986 | Nelson . | |
| 4,762,320 | 8/1988 | Larsen | 273/54 B X |
| 4,961,418 | 10/1990 | McLaurin-Smith | 128/157 |

FOREIGN PATENT DOCUMENTS

| | | |
|---|---|---|
| 45647 | 10/1970 | Fed. Rep. of Germany . |
| 1578667 | 6/1973 | Fed. Rep. of Germany . |
| 3006362A1 | 8/1981 | Fed. Rep. of Germany . |
| 3707956 | 10/1987 | Fed. Rep. of Germany . |
| 3631253 | 3/1988 | Fed. Rep. of Germany . |
| 8625798.6 | 10/1988 | Fed. Rep. of Germany . |
| 88113647 | 12/1988 | Fed. Rep. of Germany . |

Primary Examiner—Richard J. Apley
Assistant Examiner—Linda C. M. Dvorak

[57] ABSTRACT

An elastic bandage having a tubular shape with an opening for a thumb disposed therein. The bandage is adapted to be disposed about the top, bottom and both sides of the hand. It is characterized by a profiled padding on opposite sides of the bandage and is adapted to engage the opposite sides of the hand and wrist. The padding tapers into unpadded portions of the bandage in the regions between the sides of the hand and the top and the bottom of the hand so that the bandage urges against the top and the bottom of the hand with only slight pressure in the unpadded regions. The padding acts like pillars supporting the bandage which spans the space between them.

8 Claims, 1 Drawing Sheet

ELASTIC WRIST BANDAGE

FIELD OF THE INVENTION

The invention relates to an elastic wrist bandage in tubular form with a thumb opening.

SUMMARY OF THE PRIOR ART

Such wrist bandages are known for example from DE-Gbm 87 07 956 and are extensively used to support the wrist.

SUMMARY OF THE INVENTION

It is the object of the invention to improve such a wrist bandage in that the bandage is used substantially exclusively for its supporting function. According to the invention, the support is accomplished by a profiled padding disposed about the sides of the bandage but not on the middle region of the back of the hand or the palm merging into the lower arm in each case, the profile of the padding merging into the unpadded portions in the marginal region so that the bandage material bears against the soft parts under only light pressure in the region of the unpadded portions.

In this manner, the action of pressure originating from the bandage on the wrist is concentrated on the regions beside the back of the hand and beside the palm of the hand, which are largely insensitive to pressure. This essentially means placing pressure on the narrow sides of the hand, the wrist and of the adjacent region of the lower arm. As a result of their anatomical formation, they are considerably less sensitive to pressure than the regions of the back of the hand and the palm of the hand. In addition, as a result of the padding, the pressure on these narrow sides is largely equalized so that it does not feel uncomfortable. As a result of leaving unpadded the middle region of the back the hand and of the palm of the hand from the effect of the padding so as to produce only a light pressure, the effect is achieved, while maintaining the supporting function of the bandage, that as a result of the profiled padding, on the one hand blood vessels and on the other hand nerves are kept practically free of pressure so that the wrist is not disadvantageously influenced with regard to its blood and nerve supply. The blood vessels which can be influenced by pressure actually lie largely in the middle region of the back of the hand and the nerves in the middle region of the palm. This was not taken into consideration in the wrist bandages hitherto known so that when they were used, although a supporting function was achieved, an obstruction of the blood supply and impairing of the nerve function resulted as unwanted side-effects.

The padding may appropriately be constructed from a strip of elastic material incorporated in the bandage along each narrow side of the joint, and supports, as a pillar, the bandage material spanning the back of the hand and the palm of the hand like a bridge. Such strips can be processed with the bandage material in a favourable manner, for example by adhesion or welding on. The strips of elastic material, for example silicone rubber, cause, as a result of their material properties, an equalization of the pressure exerted on the narrow sides of the joint so that pressure points which would feel uncomfortable as a result are largely avoided. In addition, this effect can be made still more intense as a result of the fact that the padding comprises depressions at its side adjacent to the body, which leave room for bone projections. These depressions are preferably provided in the region of the styloid processes of ulna and radius.

BRIEF DESCRIPTION OF THE DRAWINGS

One embodiment of the invention is illustrated in the Figures.

DESCRIPTION OF THE PREFERRED EMBODIMENTS

Figure 1:
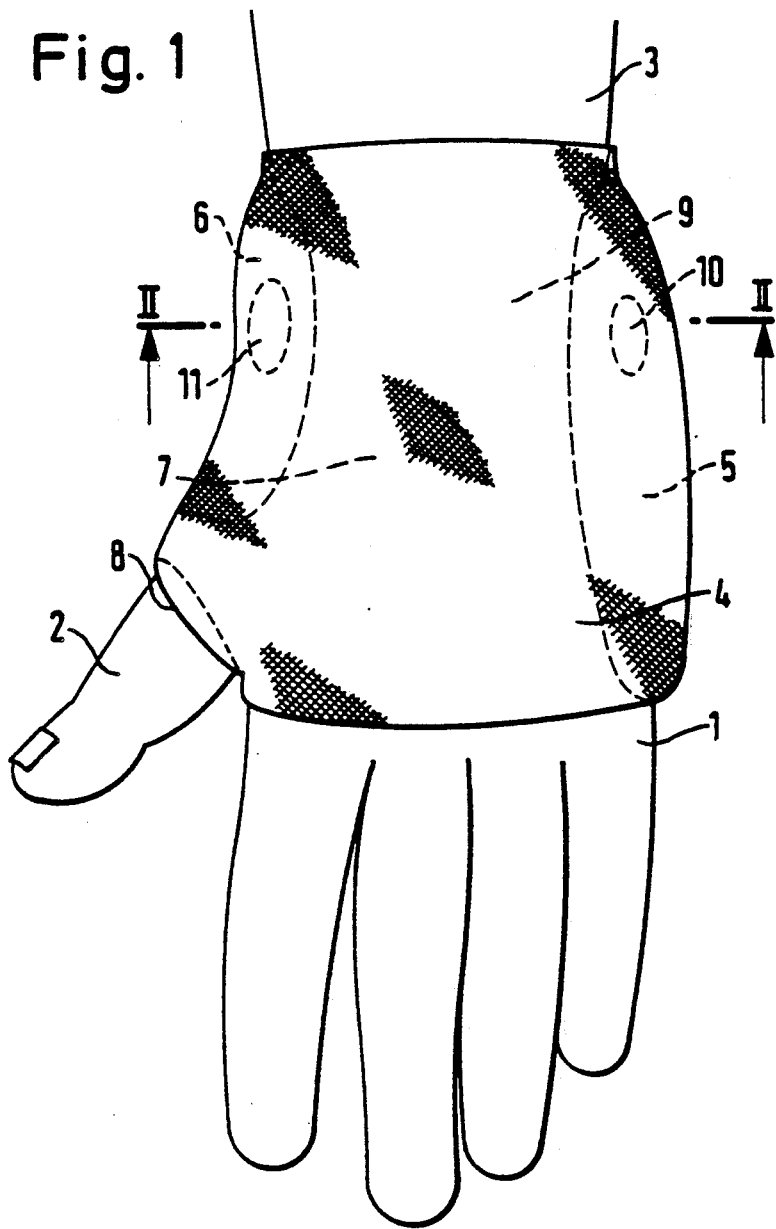
FIG. 1 shows a wrist bandage pulled onto a hand, seen at the flat side of the hand.

In FIG. 1, a human hand 1 with thumb 2 and lower arm 3 is illustrated with, pulled over the wrist 9, a resilient wrist bandage 4 which extends over the actual wrist 9 as far as the middle of the hand and the part of the lower arm 3 following on the wrist. No distinction is made between the back of the hand and the palm of the hand in FIG. 1 since the hand illustrated may be a right or a left hand. The wrist bandage 4 is provided with a thumb opening 8 for the passage of the thumb 2. The wrist bandage 4 consists of a known elastic textile material. Incorporated at each of the narrow sides of the joint is a padding in the form of strips 5 and 6, which extends substantially along the whole wrist bandage but leaves out the middle regions of the palm and back of the hand 7.

Figure 2:
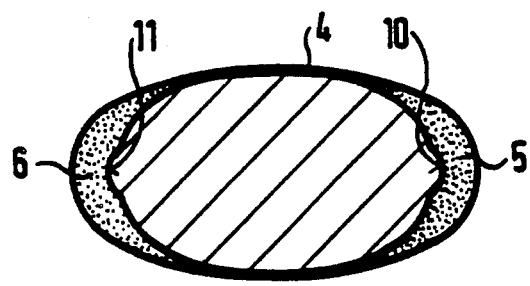
FIG. 2 shows a section on the line II—II of FIG. 1.

The shape of the strips 5 and 6 serving as profiled padding can be seen from FIG. 2. This shows a section on the line II—II in FIG. 1. According to this, the strips 5 and 6 surround the respective narrow side of the joint in sickle-shape in cross-section in such a manner that the regions of the bandage 4 connecting the tapering ends of the sickle-shaped cross-section in a bridge-like manner bear with only light pressure against the soft parts of the wrist 9 and of the adjacent parts of the body.

As a result of this formation and profiling of the strips 5 and 6 serving as padding, a lateral pressure results on the two narrow sides of the joint without any appreciable pressure being exerted on the middle regions of the back of the hand and the palm of the hand 7. Consequently, the blood circulation and the nerve function remain largely unimpaired when this wrist bandage 6 is worn.

As a result of the formation of the strips 5 and 6 of elastic material, these distribute the pressure uniformly over the narrow sides of the joint which, on the one hand benefits the supporting function of the wrist bandage 6 and on the other hand prevents the development of pressure points which feel uncomfortable. In addition, in the embodiment shown in FIGS. 1 and 2, depressions 10 and 11 are provided in the strips 5 and 6 and receive the bone projections on ulna and radius.

We claim:

1. An elastic wrist bandage (4) formed of an elastic textile material in tubular form with a thumb opening (8), characterized by profiled padding means (5,6) disposed oppositely to each other which leaves out the middle region of the back of the hand and the palm of the hand (7) including the adjacent parts of the lower arm, the profile of the padding means (5,6) merging into unpadded portions in regions between the profiled padding means (5,6) so that only the bandage material bears against the portions of the back of the hand and the palm under only slight pressure in the region of the unpadded portions.

2. A wrist bandage according to claim 1, characterized in that the padding means is formed of strips (5,6) of elastic material incorporated in the bandage and supports, as pillars, the bandage material spanning the back of the hand and palm of the hand (7) like a bridge.

3. A wrist bandage according to claim 1, characterized in that the padding comprises, at its inner surfaces, depressions (10,11) leaving room for bone projections.

4. A wrist bandage according to claim 2 characterized in that the padding comprises, at its inner surfaces, depressions leaving room for bone projections.

5. An elastic wrist bandage formed of an elastic textile material and having a tubular shape with an opening for a thumb disposed therein, said bandage adapted to be disposed about the top, bottom and both sides of a hand and wrist, said bandage characterized by a profiled padding on opposite sides of the bandage and adapted to engage the sides of the hand and wrist, said padding tapering into unpadded portions of the bandage in the regions between the sides of the hand and wrist, and the top and the bottom of the hand and wrist, so that the bandage urges against the top and bottom of the hand and wrist with only slight pressure in the region of the unpadded portions.

6. The wrist bandage according to claim 5 wherein the padding is formed of strips of elastic material attached to the bandage on each narrow side of the hand and supports, as pillars, the bandage material spanning the back of the hand and the palm in a bridge-like manner.

7. The wrist bandage according to claim 5 wherein the padding further includes depressions on the inside thereof to receive bony projections of the hand.

8. The wrist bandage according to claim 6 wherein the strips of padding are sickle-shaped in cross-section, whereby the central areas are thick and the edges are tapered.

* * * * *